United States Patent
Ouchi

[11] Patent Number: 6,165,124
[45] Date of Patent: Dec. 26, 2000

[54] FORCEPS PLUG OF AN ENDOSCOPE

[75] Inventor: Teruo Ouchi, Saitama, Japan

[73] Assignee: Asahi Kogaku Kogyo Kabushiki Kaisha, Tokyo, Japan

[21] Appl. No.: 09/252,219

[22] Filed: Feb. 18, 1999

[30] Foreign Application Priority Data

Feb. 23, 1998 [JP] Japan .................................. 10-039874

[51] Int. Cl.[7] .................................................. A61B 1/00
[52] U.S. Cl. ........................................................ 600/154
[58] Field of Search ................................. 600/154, 159; 604/167

[56] References Cited

U.S. PATENT DOCUMENTS

| | | | |
|---|---|---|---|
| 4,270,525 | 6/1981 | Furihata | 600/159 |
| 4,412,531 | 11/1983 | Chikashige | 600/104 |
| 4,649,904 | 3/1987 | Krauter et al. | 600/154 |
| 4,653,477 | 3/1987 | Akui et al. | 600/154 |
| 4,715,360 | 12/1987 | Akui et al. | 600/154 |
| 4,809,679 | 3/1989 | Shimonaka et al. | 600/154 |
| 4,920,953 | 5/1990 | McGown | 600/154 |
| 4,972,828 | 11/1990 | Ito . | |
| 5,456,284 | 10/1995 | Ryan et al. | 137/522 |

FOREIGN PATENT DOCUMENTS

| | | |
|---|---|---|
| 59-196204 | 12/1984 | Japan . |
| 60-37302 | 3/1985 | Japan . |

*Primary Examiner*—John P. Leubecker
*Attorney, Agent, or Firm*—Greenblum & Bernstein P.L.C.

[57] ABSTRACT

A forceps plug of an endoscope includes a elastic seal member provided at an inlet of a channel through which a treatment tool is to be inserted and having an opening normally closed, and a tubular guide detachably inserted into the opening so that the outer circumference thereof is brought into contact with the opening.

9 Claims, 5 Drawing Sheets

FORCEPS PLUG OF AN ENDOSCOPE

BACKGROUND OF THE INVENTION

1. Field of the Invention

The present invention relates to a forceps plug of an endoscope for closing an inlet of a channel through which a treatment tool is inserted.

2. Description of the Related Art

In the forceps plug of an endoscope, there is usually provided an elastic seal member. The seal member has an opening structured by a slit or the like. The seal member is normally closed and it can be spread open by inserting a treatment tool into the opening. The seal member can assume many and diverse shapes.

Treatment tools of an endoscope to be inserted into the forceps plug are versatile and include forceps, a snare, a syringe, a basket and a medium injection tube. Such treatment tools are roughly divided into two groups, one using a metallic coil pipe as a shaft and the other using a flexible tube made of a synthetic resin.

The coil pipe has comparatively high stiffness and problems are less likely to occur when it is inserted into or detached from the forceps plug. On the other hand, since the flexible tube does not have high stiffness, the flexible tube will be bent by the resistance developed when the flexible tube is passed through the slit formed in the seal member of the forceps plug, so that the flexible tube become no longer function.

SUMMARY OF THE INVENTION

An object, therefore, of the present invention is to provide a forceps plug of an endoscope through which even treatment tools that do not have a stiff shaft can be smoothly passed without bending extremely.

The stated object of the invention can be attained by a forceps plug of an endoscope including: an elastic seal member provided at an inlet of a channel through which a treatment tool is to be inserted, the seal member having an opening normally closed; and a tubular guide detachably inserted into the opening so that the outer circumference thereof is brought into contact with the opening.

The tubular guide may have such an inside diameter as to permit the passage of the treatment tool and maintain the pressure of the inside of the channel.

The tubular guide may be formed of either a hard elastic member or a rigid body. A flange may be formed so as to project from said tubular guide at an operator-side end that is the closest to the operator. The forceps plug may be provided with a string member for connecting said tubular guide to the vicinity of the inlet of the channel through which the treatment tool is to be inserted.

The tubular guide may be formed in such a length that when it is inserted into said closure, it at least penetrates the latter to be exposed on the opposite side.

The opening at the inlet of the tubular guide may be formed in such a shape that it progressively flares outwardly.

The present disclosure relates to the subject matter contained in Japanese patent application No. Hei.10-39874 filed on Feb. 23, 1998 which is expressly incorporated herein by reference in its entirety.

DESCRIPTION OF THE PREFERRED EMBODIMENTS

Several forceps plugs of the invention will now be described with reference to the accompanying drawings.

Figure 7:
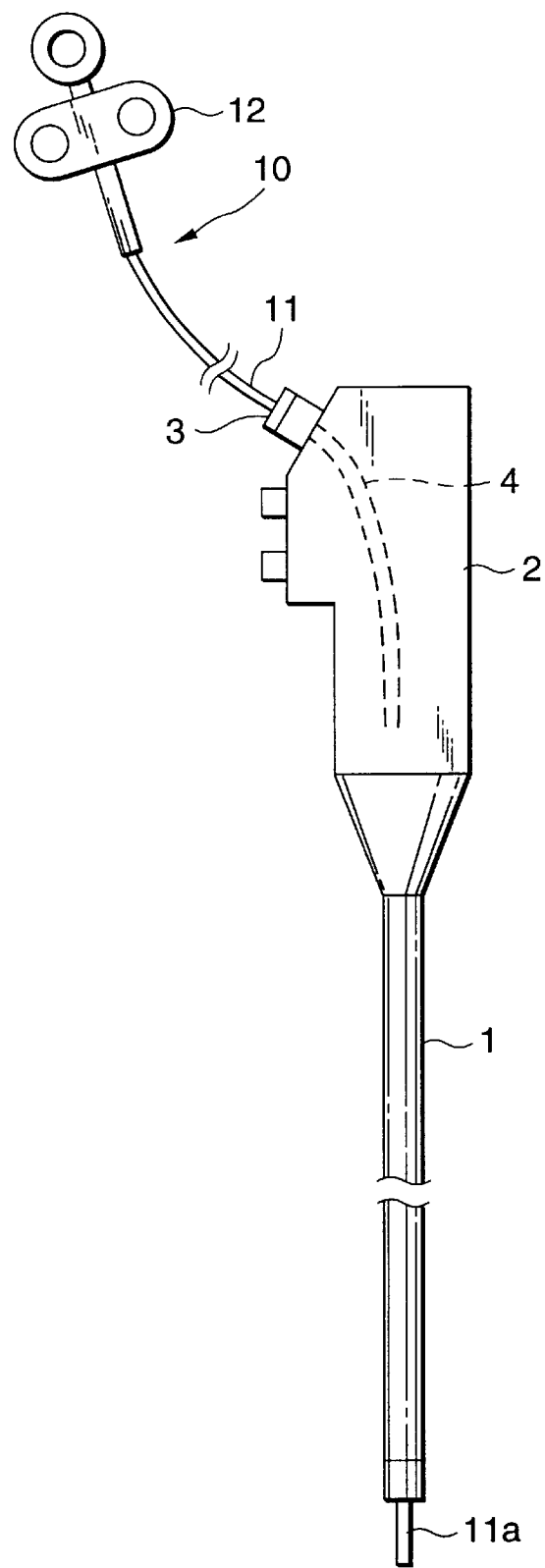
FIG. 7 is an exterior view of an endoscope having a treatment tool set in it.

FIG. 7 shows a state that a treatment tool 10 has been inserted into a treatment tool insertion channel 4 of an endoscope. An inserting portion 1 of the endoscope has a basal end connected to a manipulating section 2. A forceps plug 3 is mounted on the inlet of the manipulating section 2 from which the channel 4 extends toward the inserting portion 1.

A sheath 11 of the treatment tool 10 inserted into the channel 4 has a distal tip 11a projecting forward from a distal end of the inserting portion 1 of the endoscope. Reference numeral 12 designates a hand operated manipulating section connected to a basal end of the sheath 11.

Figure 1:
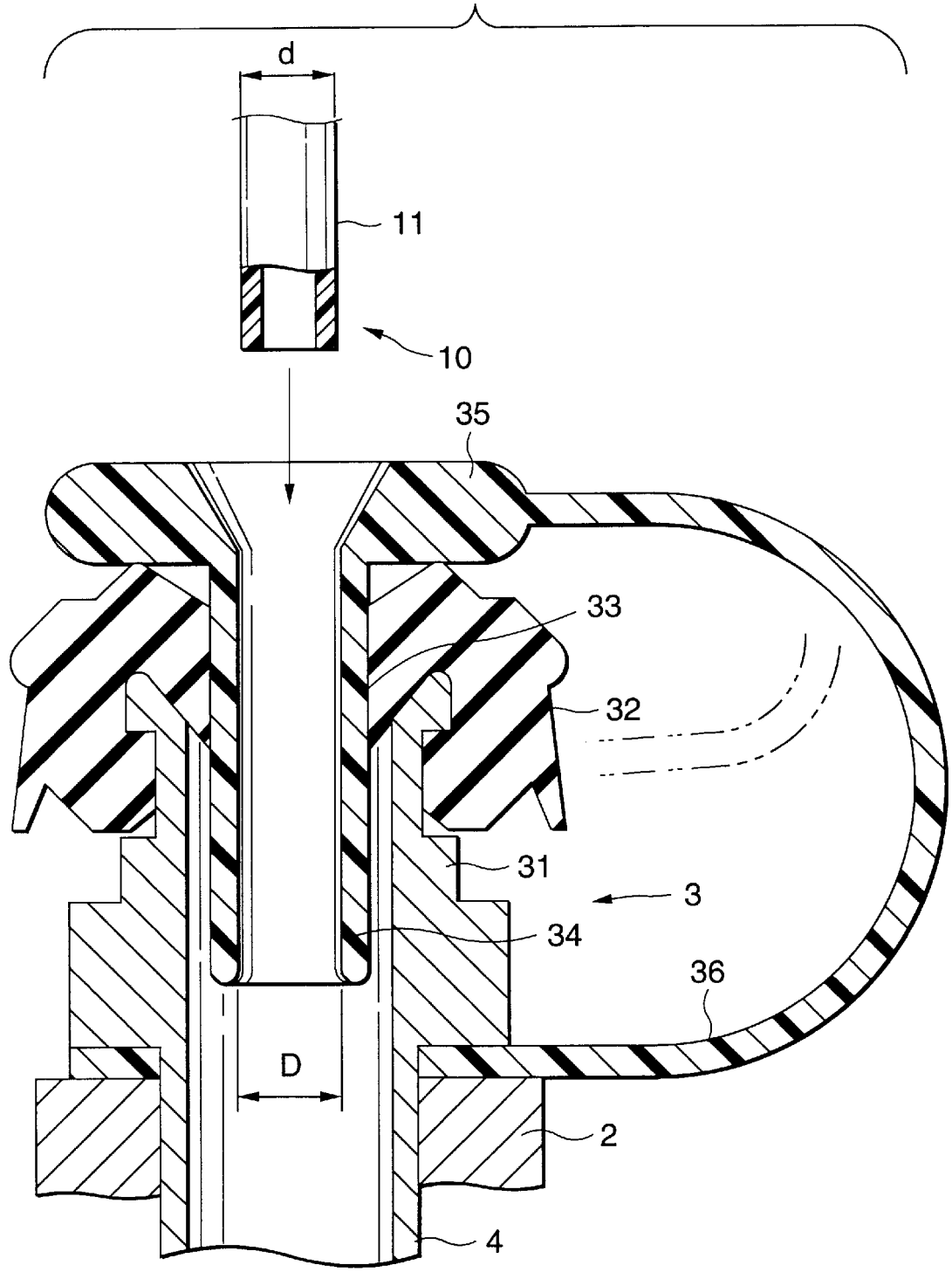
FIG. 1 is a longitudinal section view of a first forceps plug of an endoscope, showing a state that a tubular guide is inserted into the forceps plug.
Figure 2:
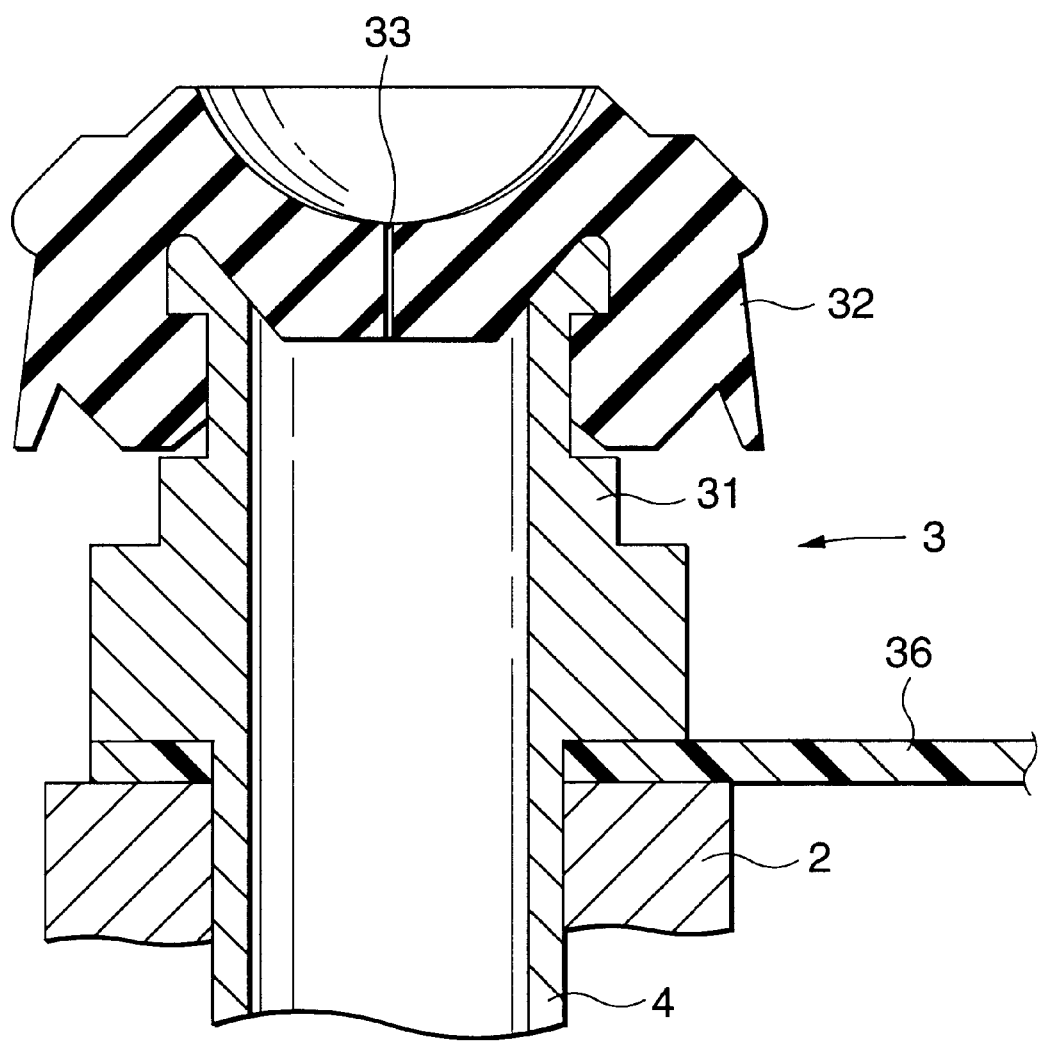
FIG. 2 is a longitudinal section view of the first forceps plug of the endoscope, showing a state that the tubular guide is not inserted into the forceps plug.

FIGS. 1 and 2 show the enlarged forceps plug 3. Reference numeral 31 designates a treatment tool insertion socket that communicates with the channel 4 and projects from the surface of the manipulating section 2. A rubber valve 32 that is elastic enough to serve as a plug is detachably fitted at the end of the socket 31 that is the closest to the operator.

A slit 33 (opening) is formed in the center of the rubber valve 32. Normally, the slit 33 is completely closed under the pressure exerted by the socket 31 and due to its own elasticity (see FIG. 2). Hence, sufficient seal is ensured even if the pressure in the channel 4 communicating with a body cavity increases to a level of some degree.

If the treatment tool (not shown) to be used has a stiff sheath, the slit 33 is spread open by the treatment tool, so as to insert the sheath into the channel 4. Accordingly, the treatment tool having the stiff sheath can be used with only a small air leakage from the channel 4.

If the treatment tool to be used has a less stiff sheath, a tubular guide 34 is inserted into the slit 33 from outside as shown in FIG. 1. The tubular guide 34 has such an outside diameter that the inserted guide 34 establishes intimate contact between its outer circumference and the inner surface of the slit 33, when the tubular guide 34 is inserted into the slit 33 while spreading the slit 33 open. If the tubular guide 34 is withdrawn from the slit 33, the slit 33 returns to the closed state under its own elasticity.

The tubular guide 34 is formed of a hard elastic member, such as a plastic material having a hardness of some degree. If desired, the tubular guide 34 may be formed of a rigid body such as a metal pipe.

A flange 35 is integrally formed with the tubular guide 34 at an operator-side end that is the closest to the operator. The tubular guide 34 is positioned in the center of the flange 35 and the opening at its inlet is formed in a taper shape gradually flared outwardly.

The tubular guide 34 is formed in such a length that it at least penetrates the slit 33 and an end of the tubular guide 34 projects from the slit 33 toward the inside of the socket 31 (for example, in a length of 5 to 20 mm). The inside diameter of the tubular guide 34 is set to have such a minimum size as to permit the passage of the sheath 11 of the treatment tool 10. In other words, the inside diameter D of the tubular guide 34 is only slightly larger than the outside diameter d of the sheath 11 of the treatment tool 10 and, from a practical viewpoint, the inside diameter D is substantially the same dimension as the outside diameter d.

Accordingly, when the sheath 11 of the treatment tool 10 is inserted into the tubular guide 34 after the tubular guide 34 has been set into the slit 33 of the rubber valve 32, the sheath 11 can be introduced into the channel 4 without substantial resistance (and, hence, without the bending of the sheath 11). In addition, the air within the channel 4 will leak only negligibly from the gap between the tubular guide 34 and the sheath 11, and thus, the pressure within the channel 4 is maintained uniformly.

The flange 35 has a thin string member 36 that is formed as an integral connecting part of the flange 35. An end of the string member 36 is fixed to the basal end of the socket 31. Therefore, if the tubular guide 34 need not be used, it is suspended near the socket 31 and when in need, it can be promptly inserted into the slit 33.

It should be noted that the string member 36 may be connected to the rubber valve 32 or other peripheral part as indicated by two-dot chain line in FIG. 1. If desired, the string member 36 may be entirely omitted without any problem.

The main aspect of the present invention lies in providing the tubular guide 34 described above. As for the rubber valve 32 and the slit 33 into which the tubular guide 34 is to be inserted, they may be of any type and shape as long as there is provided an elastic seal member with an opening that is normally closed and is spread open by the treatment tool to be inserted. Two such modifications are described below.

Figure 3:
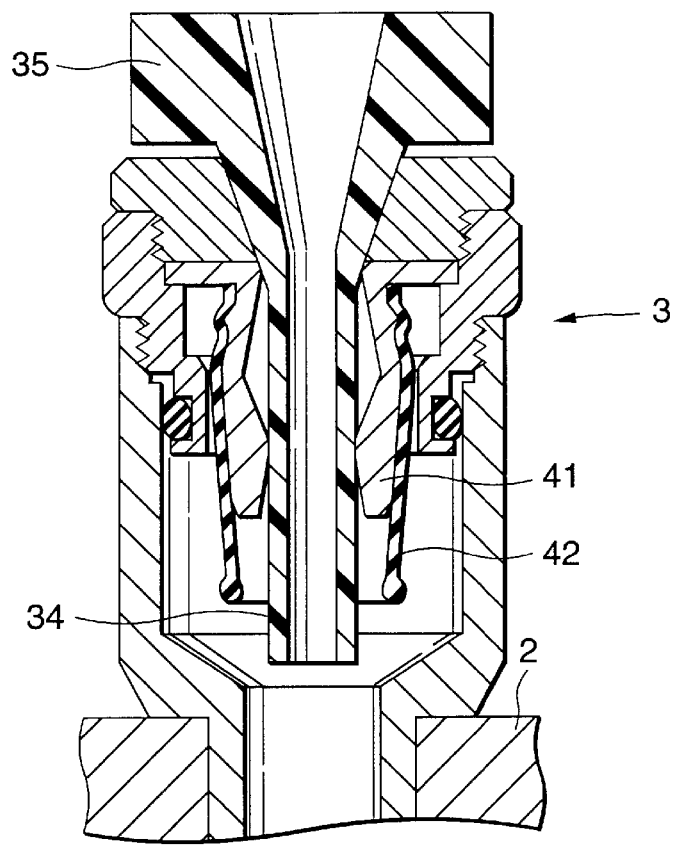
FIG. 3 is a longitudinal section view of a second forceps plug of an endoscope, showing a state that a tubular guide is inserted into the forceps plug.
Figure 4:
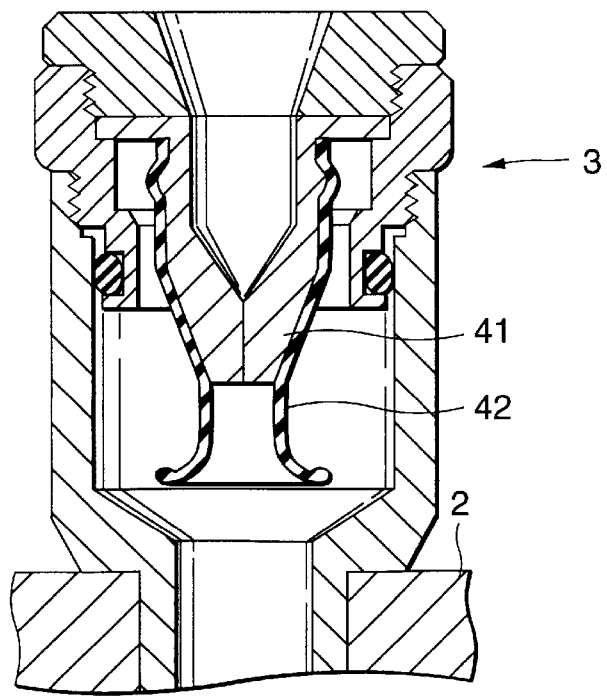
FIG. 4 is a longitudinal section view of the second forceps plug of the endoscope, showing a state that the tubular guide is not inserted into the forceps plug.

FIGS. 3 and 4 illustrate a second forceps plug 3 of such a type that a pair of columnar closing portions 41 is elastically clamped in all directions by a surrounding elastic tube 42. FIG. 3 shows a state that the tubular guide 34 has been inserted between the two closing portions 41. FIG. 4 shows a state that the tubular guide 34 is not inserted.

Figure 5:
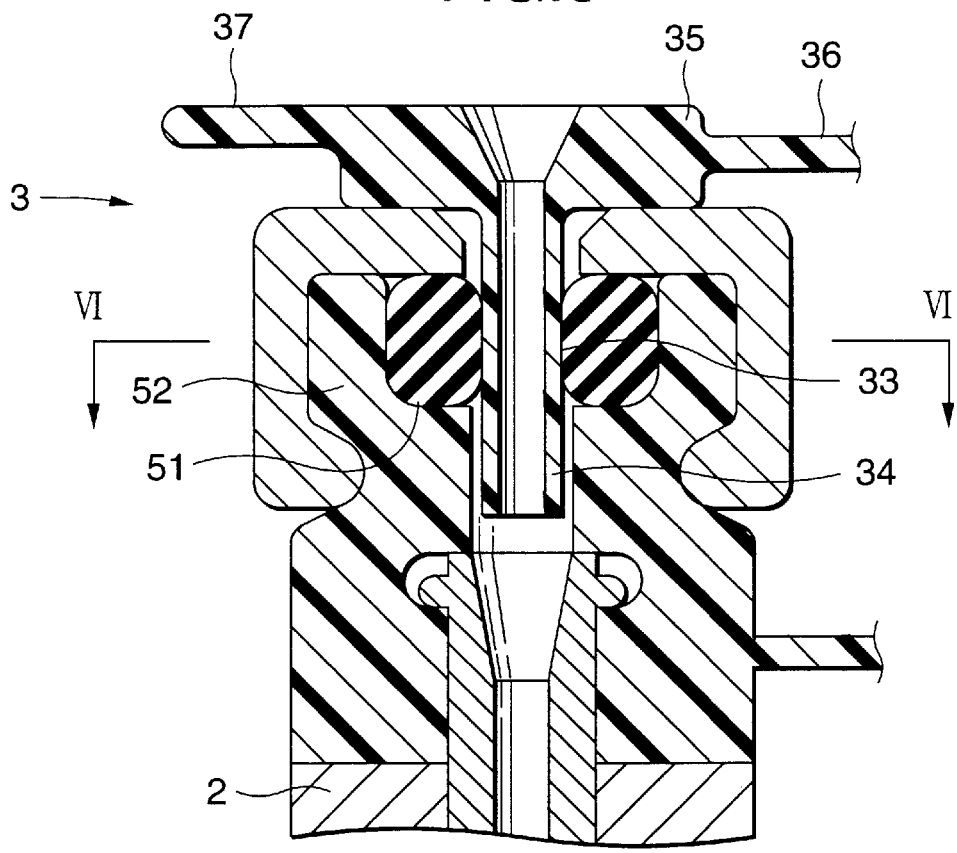
FIG. 5 is a longitudinal section view of a third forceps plug of an endoscope, showing a state that a tubular guide is inserted into the forceps plug.
Figure 6:
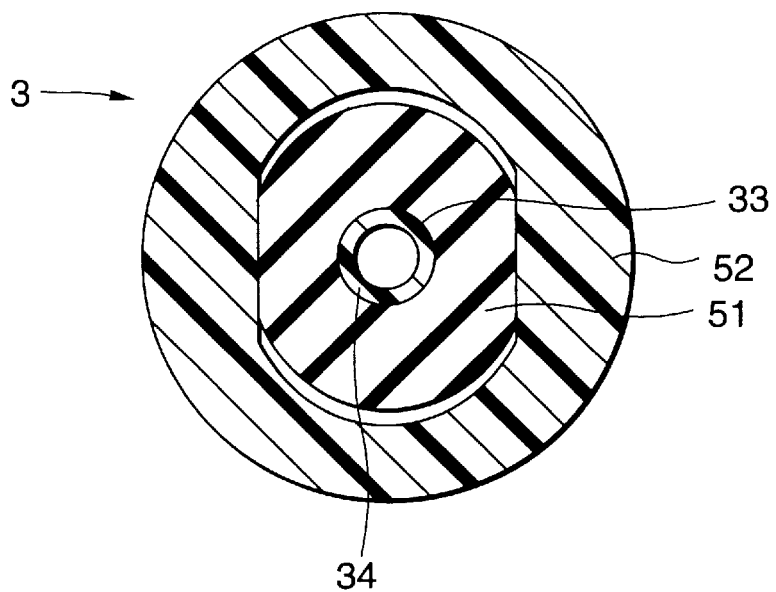
FIG. 6 is a section view of the third forceps plug taken along line VI—VI in FIG. 5.

FIGS. 5 and 6 illustrate a third forceps plug 3 of such a type that annular elastic member 51 is compressed from opposite sides by a pressing member 52 so as to close an opening 33 in the center of the elastic member 51. FIG. 5 is a longitudinal section view showing the tubular guide 34 that has been inserted into the opening 33. FIG. 6 is a section view taken along line VI—VI of FIG. 5. Reference numeral 37 designates a tab projecting from the flange 35 and the user may hold the tab 37 to pull the tubular guide 34 out of the opening 33.

According to the present invention, the tubular guide is inserted into the opening formed in the seal member of the forceps plug in such a way that the opening normally closed is spread open by the treatment tool to be inserted; as a result, the treatment tool can be smoothly passed into the forceps plug without bending extremely even if the treatment tool does not have a stiff shaft. If the treatment tool has a stiff shaft, the tubular guide may be removed and the forceps plug can be used as a related type of a state that the treatment tool can be passed into the forceps plug with no air leakage.

What is claimed is:

1. A forceps plug of an endoscope, comprising:

an elastic seal member provided at an inlet of a channel through which a treatment tool is to be inserted, said seal member having an opening normally closed; and a tubular guide detachably inserted into said opening so that the outer circumference thereof is brought into contact with said opening, and wherein said tubular guide is formed of a hard elastic member that is harder than said elastic sealing member.

2. The forceps plug according to claim 1, wherein the tubular guide has an inside diameter at most only slightly larger than an outer diameter of the treatment tool so as to permit the passage of the treatment tool and maintain the pressure of the inside of the channel.

3. The forceps plug according to claim 1, wherein an inside diameter of said tubular guide is substantially the same as an outer diameter of the treatment tool.

4. The forceps plug according to claim 1, wherein said tubular guide has a length such that when said tubular guide is inserted into said opening, said tubular guide at least penetrates said opening and an end of said tubular guide projects downwardly through said opening and into the channel.

5. A forceps plug of an endoscope, comprising:

an elastic seal member provided at an inlet of a channel through which a treatment tool is to be inserted, said seal member having an opening normally closed; and a tubular guide detachably inserted into said opening so that the outer circumference thereof is brought into contact with said opening, and wherein said tubular guide is formed of a rigid body.

6. A forceps plug of an endoscope, comprising:

an elastic seal member provided at an inlet of a channel through which a treatment tool is to be inserted, said seal member having an opening normally closed; and a tubular guide detachably inserted into said opening so that the outer circumference thereof is brought into contact with said opening, and wherein said tubular guide has a flange projecting laterally from an operator-side end of said tubular guide.

7. A forceps plug of an endoscope, comprising:

an elastic seal member provided at an inlet of a channel through which a treatment tool is to be inserted, said seal member having an opening normally closed; and a tubular guide detachably inserted into said opening so that the outer circumference thereof is brought into contact with said opening; and a string member for connecting said tubular guide to the vicinity of the inlet of the channel through which the treatment tool is to be inserted.

8. The forceps plug according to claim 7, wherein said string member is attached to either said seal member or the inlet of the channel.

9. A forceps plug of an endoscope, comprising:

an elastic seal member provided at an inlet of a channel through which a treatment tool is to be inserted, said seal member having an opening normally closed; and a tubular guide detachably inserted into said opening so that the outer circumference thereof is brought into contact with said opening, and wherein an opening at an inlet of said tubular guide is formed in a taper shape progressively flared outwardly.

* * * * *